United States Patent [19]

Bernard et al.

[11] Patent Number: 5,773,617
[45] Date of Patent: Jun. 30, 1998

[54] DEALLYLATION REAGENT AND DEALLYLATION METHOD USING SAID REAGENT

[75] Inventors: Jean-Marie Bernard, Mornant; Errol Blart, Maison-Alfort; Jean-Pierre Genet, Verrières-le-Buisson; Sandrine Lemaire-Audoire, Neuilly-sur-Seine; Monique Savignac, Gify/Yvette, all of France

[73] Assignee: Rhone-Poulenc Chimie, Courbevoie Cedex, France

[21] Appl. No.: 532,630

[22] PCT Filed: Apr. 8, 1994

[86] PCT No.: PCT/FR94/00397

§ 371 Date: Feb. 22, 1996

§ 102(e) Date: Feb. 22, 1996

[87] PCT Pub. No.: WO94/24088

PCT Pub. Date: Oct. 27, 1994

[30] Foreign Application Priority Data

Apr. 9, 1993 [FR] France ................................ 93 04233

[51] Int. Cl.$^6$ .......................... C07C 209/62; C07K 1/06; C07K 1/12
[52] U.S. Cl. .......................... 544/401; 530/335; 530/336; 530/337; 546/217; 546/245; 548/492; 560/38; 560/155; 564/321; 564/364; 564/383; 564/391; 564/392; 564/461; 564/462; 556/13
[58] Field of Search ...................................... 530/335, 336, 530/337; 544/401; 546/217, 245; 548/492; 560/38, 155; 564/321, 364, 383, 391, 392, 461, 462; 556/13

[56] References Cited

FOREIGN PATENT DOCUMENTS

| 194554 | 9/1986 | European Pat. Off. . |
|---|---|---|
| 407256 | 1/1991 | European Pat. Off. . |
| 518295 | 12/1992 | European Pat. Off. . |
| 566459 | 10/1993 | European Pat. Off. . |
| WO 92/19643 | 11/1992 | WIPO . |

OTHER PUBLICATIONS

Noyori et al., Chemical Abstracts, vol. 109, abstract 129602w, 1988.
Kamber et al., Canadian Journal of Chemistry, vol. 63, No. 4, pp. 823–827, 1985.

Primary Examiner—Richard L. Raymond
Attorney, Agent, or Firm—Burns, Doane, Swecker & Mathis, L.L.P.

[57] ABSTRACT

The present invention relates to a reagent and to a process which are useful, when carrying out an organic synthesis, for cleaving an allylic group from a function which is protected with the latter.

This reagent is defined in that it contains:
a) a solvent system;
b) a catalyst containing at least one element from column VIII of the Periodic Table of the Elements, the said element from column VIII of the Periodic Table being coordinated with at least one coordination agent which is soluble in the said solvent system;
c) a compound which is at least partially soluble in the said solvent system and which contains at least one nucleophilic function.

Application to organic synthesis.

28 Claims, No Drawings

DEALLYLATION REAGENT AND DEALLYLATION METHOD USING SAID REAGENT

The present application is a 371 of PCT/FR94/00397, filed Apr. 8, 1994.

The present invention relates to a reagent and to a process which are useful, when carrying out an organic synthesis, for cleaving an allylic group from a function protected by the latter.

It is common to protect a molecule by blocking the functions which, under the operating conditions envisaged, would be reactive or would be considered to be reactive, by groups described as being protecting groups.

These techniques are particularly useful during peptide syntheses or syntheses on (poly)nucleotides, and the functions most commonly protected are the acid, alcohol, amine or thiol functions.

These protection techniques are especially used for the synthesis of complex molecules such as peptides of at least 2 amino acids, usually of at least three, or when complex amino acids are used, that is to say those which have a function containing labile hydrogen (amine, alcohol including phenol, nitrogen-containing ring, thiol, etc.) in addition to an acid function and in addition to an amine function. They are also useful for nucleotides, nucleosides, polynucleotides and polynucleosides. A protecting group may also be useful for molecules having at least six, and advantageously twelve, carbon atoms, or for molecules which possess several functions, at least two and, advantageously, three functions.

Among the groups most commonly used, there may be mentioned the BOC or tert-butyloxycarbonyl group, Z or benzyloxy groups, or even the FMOC group. It should be pointed out that groups of allylic structure would have been considered as being potentially very valuable if suitable cleavage means were available.

To date, the only protecting groups of allylic type which are used are allyloxycarbonyl groups, the removal of which has been dealt with in previous applications (in particular the application filed in France under No. 92/04621 and the corresponding European application) by the Applicant and which should not be confused with the allyl derivatives according to the present application; these allyloxycarbonyl derivatives have a carbonyl function derived from an acid function, which makes the cleavage easier.

The deprotection usually used is lysis in an acidic medium, generally in an anhydrous hydrohalic medium (that is to say one with a water content generally of less than 1%, advantageously of less than $10^{-3}$ and preferably of less than $10^{-4}$).

However, this technique has a number of drawbacks. The cleavage reaction is sometimes slow or requires large excesses of reagent. Alkoxy groups have a tendency to be converted into carbocation with a change towards double bonds when this is possible, or towards alkylation reactions on the ring, which is particularly inconvenient in the case of syntheses of peptides whose sequence contains nucleophilic residues such as aromatic rings (tryptophan, tyrosine, etc.) or sulphur-containing residues (methionine).

This technique is not applicable in the case of allylic groups, which is why these groups, which otherwise would have numerous advantages, are not used.

Accordingly, one of the aims of the present invention is to provide a process and a reagent which allow the cleavage of an allylic protecting group from the function which it protects.

Another aim of the present invention is to provide a process and a reagent which avoid the alkylation reactions of aromatic rings.

Another aim of the present invention is to provide a process and a reagent which avoid the alkylations of function(s) belonging to the same molecule and described as being nucleophilic.

These aims and others which will emerge in the following text, are achieved using a reagent which is useful for cleaving allylic, so-called protective, groups. From the functions which it is supposed to protect.

The reagent according to the present invention contains:

a) a solvent system;
b) a catalyst containing at least one element from column VIII of the Periodic Table of the Elements, the said element from column VIII of the Periodic Table being coordinated with at least one coordination agent which is soluble in the said solvent system;
c) a compound which is at least partially soluble in the said solvent system and which contains at least one nucleophilic function.

The solvent system may be a one-phase system or a two-phase system (that is to say one with an aqueous liquid phase and an organic phase).

In the case of a two-phase system, when the substrate and/or the supply product are sparingly soluble in the aqueous phase, it is possible to carry out the reaction, on the one hand, by adding an intermediary solvent B, or on the other hand, in a multiphase system, either with or without addition of a solvent A, or with simultaneous addition of an intermediary solvent B and solvent A.

The solvents A are organic solvents chosen such that they dissolve at least 1%, advantageously at least 2%, preferably 5%, by mass of the substrate and are sufficiently hydrophobic to be water-immiscible in all proportions.

It is preferable for water to be able to dissolve at most only 10% of solvent A, advantageously at most 1%, by mass, even in the presence of the substrate as an intermediary solvent.

It is preferable for the solvent A to be able to dissolve at most only 10% of water, advantageously at most 1%, by mass, even in the presence of the substrate as an intermediary solvent.

The solvents A may be mixtures, including petroleum fractions. Naturally, under the operating conditions, the solvents A must be inert with respect to the substrates and reagents used.

In particular when the solvent system is a two-phase system, phase transfer agents, which will distribute themselves between the two phases, may be added.

The preferred families of solvents are chosen from the group consisting of hydrocarbons, aromatic derivatives, ethers, esters and halogenated solvents. If it is desired to recover the solvents, it is desirable for them to be less nucleophilic than the said nucleophilic compound, so as not to interfere with the reaction unless, of course, the said nucleophilic compound is in sufficient excess to act as (an intermediary) solvent.

By way of examples of these families, there may be mentioned, as halogenated aliphatic derivatives, dichloromethane, 1,2-dichloroethane and 1,1,1-trichloroethane, as aromatic derivatives, toluene, and as halogenated aromatic derivatives, chlorobenzene, as esters, ethyl acetate and isopropyl acetate, as ethers, tert-butyl ether and methyl ether, as well as anisole and heavy alcohols, that is to say those satisfying the immiscibility requirements as specified above.

For reasons of industrial economy, it is preferable for the solvent A to be distillable at atmospheric pressure or under primary or secondary vacuum.

Among the solvents A which should particularly be mentioned are those which are phenolic and which are detailed in the French applications filed by the Applicant under the Nos. 89/15957 and 91/12524.

According to one embodiment of the present invention, when the substrates are not water-soluble, a person skilled in the art is then at liberty to add an intermediary solvent B whose role will be to solubilize the substrate in the aqueous phase.

This intermediary solvent B will be able to be shared between aqueous and organic phases, when the latter phase exists, either initially or by virtue of the possible simultaneous use of the solvent A.

It is preferable for the water to be able to dissolve at least $1/10$ of intermediary solvent B, advantageously at least $1/3$, by mass, even in the presence of the catalyst with its coordination agents.

The intermediary solvent is advantageously added in sufficient amounts such that the amount of soluble substrate in the aqueous phase is at least of the same order of magnitude as the amount of catalyst present in the aqueous phase at the start of the reaction.

When one-phase solvent systems are used, it is possible to use the solvents which are used as intermediary solvent in the case of the two-phase system.

Thus, among the solvents which may be used as solvent or intermediary solvent, there may be mentioned water-soluble solvents of alcohol, nitrile, ether (especially cyclic ether), acid, sulphone, sulphoxide, simple or polyfunctional amide (such as urea), ester, ketone or even amine type, in particular in the case where the said nucleophilic compound also serves as (an intermediary) solvent.

Thus, it is possible to use a solvent system, which may or may not be a one-phase system, containing a hydrophilic phase (that is to say one containing a solvent, or a solvent mixture, which is miscible in any proportion and is itself miscible in large proportions, as main constituent).

The metals giving the best catalytic results are crude platinum metals, preferably those which are either isoelectronic with palladium or in a valency state which is isoelectronic with palladium (0), preferably both; however, it may be economically advantageous to use lighter metals on account of their much lower costs; within the family of crude platinum metals, each of them has specificities which make them more or less advantageous depending on the case; palladium, especially in oxidation state zero, usually gives the best results.

The said coordination agents are advantageously trivalent hydrocarbon derivatives of the elements from column VB, advantageously from a period ranking higher than the second and generally lower than the sixth, of the Periodic Table of the Elements (supplement to the Bulletin de la Société Chimique de France January 1966 No. 1). Besides those which are detailed in the following text, examples of such compounds which may be given are trivalent oxygen-containing acid derivatives (phosphorous, arsenious, antimonious and, for the record, nitrous), which derivatives are obtained in particular by esterification or by substitution of at least two of the three hydroxyls (the trisubstitution leads in fact to the pnictines which form the subject of a more detailed description).

Among the said hydrocarbon derivatives of the elements from column V, the preferred ones are those which are derived from the hydrogen pnictides by total or partial substitution of the hydrogen by hydrocarbon residues which may be connected to the atom from column V B via a double bond (as in the imines) or a triple bond (as in the nitriles).

However, the hydrocarbon derivatives of the elements from column V are advantageously derived from the hydrogen pnictides by total or partial substitution of the hydrogen by monovalent hydrocarbon residues, advantageously by alkyls [in the present description, alkyl (in French alco-yle) is taken in its etymological sense to be a hydrocarbon residue of an alco-hol (in French alco-ol) after the alcohol (or ol) function has been disregarded]; by analogy with the term pnictine, these alkyl compounds will be referred to in the present description as pnictines.

Thus, in the case of nitrogen, substitution of hydrogen nitride (ammonia) gives amines; in the case of phosphorus, substitution of hydrogen phosphide gives phosphines; in the case of arsenic, substitution of hydrogen arsenide gives arsines; and in the case of antimony, substitution of hydrogen antimonide (or stibide) gives stibines. They are advantageously chosen from hydrocarbon derivatives of phosphorus such as phosphines.

The said catalyst advantageously contains, as water-soluble coordination agent, a pnictine, a trialkylphosphine, preferably (for economic reasons) a triarylphosphine, generally a triphenylphosphine. The said phosphine and the said metal from column VIII are advantageously in the form of tetrakis phosphine metal.

When the solvent system requires it, it is useful and sometimes necessary to make the catalytic system water-soluble; in order to make the coordination agents and especially the pnictines soluble, it is convenient to graft on polar water-solubilizing groups.

Neutral groups such as polyols may be grafted on but, bearing in mind the strong lipophilicity of the pnictines, it is preferable for the grafted groups to be ionic; cationic, such as quaternary ammoniums, or anionic, such as any group forming the associated base of acids, preferably strong acids. In the latter case, the carboxylic, sulphonic and phosphonic groups may be mentioned, and more generally those giving equivalent hydrophilicity.

It is possible, in particular, to mention the groups used to modify the phosphines in order to obtain those intended in the French patent filed under No. 76/22824 and published under No. 2,366,237 or in the French patent published under No. 2,549,840.

By way of examples of water-soluble phosphines, there may be mentioned soluble triphenylphosphinetrisulphonates $P(C_6H_4—SO_3^-)_3$, for example alkali metal triphenylphosphinetrisulphonates and those of formula $P(C_6H_4—CO_2H)_3$, preferably in anionic form.

Thus, according to a particularly advantageous embodiment of the present invention, a two-phase system may be used in which one of the two liquid phases is an aqueous phase, in which the metal from column VIII is solubilized in the aqueous phase by a pnictine, or equivalent, which is water-soluble.

When there are risks of the catalyst being poisoned, that is to say when so-called "soft" nucleophiles are used, the nucleophilic function of which is generally based on metalloids from a high row at least equal to that of phosphorus or sulphur, it is preferable to use:

either pnictines, in general phosphines whose basicity is high (the basicity, which is low with triarylphosphines, increases with the number of replacements of aryl by chains in which any unsaturations [their presence is not desirable] are not conjugated with the doublets of the element from column V), such as bis- or tris (cyclohexylphosphines), for example;

or polyfunctional, generally bifunctional, pnictines which allow chelation of the metal by the pnictine functions; in general the pnictine functions are, taking the most direct route, separated by 2, 3 or 4 atoms, usually carbon atoms; the formulae of the type ω, ω'-diphenylphosphinoethane; or ω, ω'-diphenylphosphinobutane.

The two-phase technique greatly facilitates the recovery and recycling of the catalyst, this recycling being one of the key parameters of the viability of this type of process, on account of the ever-increasing price of crude platinum metals.

Within the context of the present invention, it is possible to use a metal catalyst in elemental form (oxidation state zero) or in oxidized form. These catalysts may be in the form of salts, oxides or complexes. Among the salts, oxides and complexes of the metals mentioned above, in oxidation state II, there may be mentioned palladium chlorides, palladium acetate and palladium chloride complexed with benzonitrile. It should be pointed out that the anions are fairly unimportant, only the cations count.

Among the complexes of metals in oxidation state zero, there may be mentioned dibenzylideneacetonepalladium.

It should be pointed out that the level of oxidation of the metal is not necessarily conserved in the reactor; the reason for this is that the pnictines are generally fairly reductive as regards reducing palladium to the elemental state, even when introduced in palladous form.

For better implementation of the invention, it is preferred to use an amount of catalyst such that the molar ratio between the metal catalyst and the compounds of the elements from column V, when these compounds are in the form of coordination agents, often referred to by the term ligand, are between 2 and 100, more generally from 4 to 30. These molar ratios should take into account the number of coordinating functions per molecule; thus, when molecules having two pnictine functions are used as coordination agent, the values of the above domains should be divided by two.

The amount of solvent system used is such that the concentration of the metal from column VIII is preferably greater than $10^{-5}$, advantageously from $10^{-2}$ to $10^{-3}$M in the solvent.

The said nucleophilic compound should have two characteristics; on the one hand, it should be nucleophilic, that is to say electron-rich, and on the other hand, it should be soluble in the solvent system.

In the present application, those compounds will be preferred which, on various nucleophilicity scales, have a nucleophilicity which is at least equal to that of diethylamine (see "March", 3rd edition, pp. 307–309).

Indeed, the choice of nucleophile depends on the functions to be deprotected; it is generally preferred to use, as nucleophiles, molecules bearing function(s) which is (are) at least as nucleophilic as the functions with respect to which selectivity is required.

According to a particularly advantageous embodiment of the present invention, when the reagents allow this, the functions for which alkylation is to be avoided are protonated and a nucleophile which is non-protonatable under the operating conditions is selected. In this situation, the above restriction on the nucleophilic nature becomes such that the nucleophilicity must be greater than that of the $NH_4^+$ ion. This protonation takes place in aqueous phase using acid whose pKa is at least one point lower, preferably at least 2 points lower, than the pKa of the acid associated with the nucleophilic function which it is desired to protect. An excess of at least 10% relative to the amount required for neutralization is preferable.

These nucleophilic functions are preferably those in which at least one mesomeric formula carries a hydrogen; they may be anions or neutral molecules. In order to illustrate the richness of this category of substrate, there may be mentioned in a non-limiting manner:

functions carrying divalent sulphur (such as thiol, polysulphide, thioacids, etc.), preferably those in which at least one mesomeric formula carries a hydrogen:
organic aliphatic sulphides and disulphides (containing primary, secondary or tertiary radicals) or aromatic or heterocyclic sulphides and disulphides;
thiols (free or in salt form);
carbon-containing functions capable of forming carbanions (malonic or β-diketone function for example);
pnictines (phosphines, amines, anilines, etc.), preferably secondary pnictines.

Certain functions such as primary pnictines, or molecules of malonic type such as beta-diketones, may serve several times (usually twice, as in the case of the above example) as nucleophiles and this fact should be taken into account when calculating the stoichiometric amount.

The preferred nucleophiles are those which correspond to atoms from a row of the Periodic Table at least equal to the third, such as sulphur, for example the hydrogen sulphide function.

It is desirable to perform the reaction in a Lewis acid medium, or preferably a Bronstedt acid medium, especially when the function to be deallylated is a base of pnictine type.

When the substrate does not possess a suitable acid function, it is preferable to use an acid whose pKa shows an acidity at least one unit, preferably at least two units, higher than the acidity of the acid associated with the said base. It is preferable for at least 50%, more advantageously 90%, of the said base to be in protonated form. The acid may be provided by the same molecule as the nucleophile, as is mentioned below.

When so desired, in order for it to be hydrophilic, or rather water-soluble the said nucleophilic compound should be such that, under normal conditions, water is capable of dissolving at least 0.2, advantageously 0.5 and preferably 1 gram-equivalent of nucleophilic function thereof.

It should be noted that nucleophilic reagents which would have little or no water-solubity may be rendered water-soluble by providing a highly hydrophilic function on the molecule. Strong or medium-strength acid functions (pKa at most equal to 6, advantageously to 5, preferably to 4), whether they contain sulphur (sulphonic, sulphuric monoester, etc.), phosphorus (phosphoric ester, phosphonic acid, phosphinic acid, etc.), carbon or the like, give results which are good enough to make one wonder whether any synergy is present. The best results are obtained at the present time with a carbon-containing function, namely the carboxylic function.

Thus, advantageously, the results obtained from nucleophiles in which the nucleophilic function is carried by a carbon which is postvicinal to, or preferably vicinal to, that carrying the acidic function.

In general, it is preferable for there to be, via the shortest pathway, between 3 and 7 and preferably between 4 and 6 chain members between the atom carrying the acidic hydrogen (or one of the atoms carrying the acidic hydrogen if there are several acidic functions) and the nucleophilic atom, and including these two atoms.

One of the best nucleophiles is thus thiosalicylic acid (H—S Φ—COOH) (number of chain members equal to 5), especially in monoanionic or, preferably, acidic form.

The best results are those which are obtained by association of the nucleophilic functions that are not protonatable, or are difficult to protonate, with the acidic functions. The results obtained with zwitterions are sometimes mediocre.

It is, obviously, preferable for the water and the nucleophile to be miscible in any proportion. Several nucleophilic functions may be carried within the same compound.

It is preferable for there to be at least one nucleophilic function per 10 carbon atoms, advantageously one per 8 and preferably one per 4, relative to the number of carbons.

It is also preferable to use small molecules in which the number of carbons is not significantly greater than about 10.

Lastly, it may be practical to choose a nucleophilic compound whose solubility decreases considerably with the temperature to pass to the gaseous phase, thus allowing easy removal by distillation.

In general, the said nucleophilic compound is present (initially, but more preferably at the end of the reaction) at a concentration of at least ½, advantageously 2 and preferably 5 gram-equivalents per litre.

When the nucleophilic compound has, when converted to a nucleophilic function, a low molecular weight, concentrations as high as 10 equivalents per gram are often exceeded.

If the deallylation provided by the use of the aqueous phase is not considered to be sufficient and it is desired to increase it, the excess of the said nucleophilic compound relative to the substrate may be varied in order to do this, for example by increasing the stoichiometric excess (in general considerably greater than 10%) relative to the desired reaction, in order to bring it to a value at least equal to ¼, advantageously to ½ and preferably to once the stoichiometric amount (that is to say to work with amounts respectively at least equal to ⅝; 3/2 and 2 S.A.).

Thus, advantageously according to the present invention, the amount of the said nucleophile is at least equal to 3/2 times the amount required stoichiometrically. In general, such stoichiometric excesses are only used when total deallylation is desired.

Another aim of the present invention is to provide a process which substantially accelerates the kinetics of cleavage.

Another aim of the present invention is to provide a process which avoids the alkylations of the aromatic rings.

Another aim of the present invention is to provide a process which avoids the alkylations of the functions which are described as being nucleophilic.

These aims and others, which will become apparent in the following text, are achieved using a process for the treatment of a molecule containing at least one allylic function, in which the said molecule is subjected to the reagents specified above.

Advantageously, the said molecules contain at least one allylic function corresponding to the following formula (I):

Z—C(R$_1$) (R$_2$)—C(R$_3$)══C (R$_4$) (R$_5$)     (I)

where
R$_1$ represents a hydrogen or an alkyl radical, preferably containing 1 or 2 carbon atoms;
R$_2$ represents a hydrogen or an alkyl radical, preferably containing 1 or 2 carbon atoms;
R$_3$ represents a hydrogen or an alkyl radical, preferably containing 1 or 2 carbon atoms, or, with R$_4$, forms an additional double bond;
R$_4$ represents a hydrogen or an alkyl radical, preferably containing 1 or 2 carbon atoms, or, with R$_3$, forms an additional double bond;

R$_5$ represents a hydrogen or an alkyl radical, preferably containing 1 or 2 carbon atoms, or an aryl radical;
Z being the radical derived from the molecule to protect the bond replacing a hydrogen of the function whose protection is desired, Z contains the protected molecule, which needs to be freed of its protecting group;
with the condition that Z does not form an allylic ester function with the residue of the molecule (—C(R$_1$) (R$_2$)—C(R$_3$)══C(R$_4$)R$_5$)).

Z may, obviously, contain one or more allylic ester function(s), but elsewhere in the molecule.

Since the said function to be protected is not an acidic function or equivalent,
R$_5$ may be a group referred to as "Ar" as described in the British patent filed on 31.12.1990 under No. 90/28208.8 and entitled "Protecting group".
R$_5$ and R$_4$ may be fractions of the group referred to as "Ar" in the above application, such that R$_5$ and R$_4$, as well as the carbon which carries them, forms a radical Ar as defined in the above British application.
R$_5$ may be any lipophilic group as described in the French patents in the name of the Applicant filed on 02.10.1989 under the No. 89/13054 and entitled "Procédé de solubilisation de peptides et procédé de synthèse de peptides" [Process for the solubilization of peptides and process for the synthesis of peptides] and that filed on 04.12.1989 under No. 89/15957 and entitled "Milieu reactionnel et solubilisant de peptides et procédé de synthèse utilisant ce milieu" [Reaction medium for solubilizing peptides and synthetic process using this medium].

In general, the association of the group referred to as Ar in the above British application with an allylic group by way of "L" is very favourable.

It is preferable for Z to have the structure Z'—χ— with χ being an atom from columns V or VI, advantageously V, preferably a nitrogen (which is itself advantageously alkylated such that in the final formula the nitrogen is tertiary, if it is desired to facilitate the cleavage). Z' advantageously has no carbonyl function linked to χ.

The term alkyl is taken in its etymological sense which has already been specified, with the additional note that it may also signify an aryl group.

It is preferable for at least 2, advantageously 3 and preferably 4, of the radicals R$_1$ to R$_5$ to be of not more than two carbons; however, at least one of the radicals R$_1$ to R$_5$ may be such that the allylic alcohol is a heavy alcohol, for example one from the aromatic series, of terpene type, or from the steroid series.

Thus, at least 1 radical and not more than 3 radicals R$_1$ to R$_5$ may be homo- or heterocyclic, condensed or non-condensed polycyclic aryl radicals.

Thus, the present invention makes it possible to use molecules of structure:

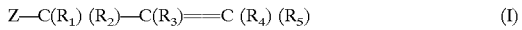

with i taking all the integer values from 1 to n
allyl$_i$ being of formula

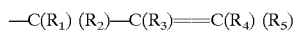

The allyl$_i$s are such that advantageously at least two, preferably 3, different formulae of allyl$_i$ are present in the molecule. It is preferable for these formulae to have respectively 0, 1 and/or 2 substituents R$_1$ to R$_5$.

N is advantageously at least equal to two and preferably to 3, and n is in general at most equal to 10 (one significant figure).

The reaction temperature is generally between the end melting point and the initial boiling point of the reaction medium, advantageously between 0° C. and 100° C., preferably between room temperature (about 20° C.) and 50° C.

It is found that the selectivity increases when the reaction is performed in two phases, but the kinetics decreases.

According to the present invention, it has been found that it is possible to use the direct allylic derivatives (direct as opposed to the allyloxycarbonyl derivatives in which, for example, the amine function is protected in the form of an allyloxycarbamate, the breaking of the ester function inducing that of the carbamic function, thereby automatically releasing the amine function), that is to say derivatives possessing no carbonyl function in a post-homoallylic position facilitating cleavage (such as, for example, in the case of allyl carboxylates), in order to protect various functions possessing a labile hydrogen. It has been proven in particular that a primary amine function can be protected using two allyl functions.

It has also been demonstrated that the various allylic functions are deallylated selectively with respect to each other. This selectivity does not act solely between variously substituted allyls, but also between identical allylic groups, for example between allyls in the strict sense or between methallyls. This property makes it possible to perform a deallylation of tertiary amines (especially those which are at least diallylated) which is selective relative to that of secondary amines (especially those which are at least monoallylated). This makes it possible in particular to perform a mono-deallylation on an atom from column V, in particular a nitrogen, when this atom carries at least two allylic functions.

Thus, by varying the nucleophilicity of the compounds receiving the allylic groups, or by varying the amount of the said receiver, it is possible to free the following allylated functions successively for the record, allyloxycarbonyl functions (for the latter, amine functions give good results as nucleophiles)

tertiary allylated functions;

secondary allylated functions.

Thus, when a deallylation which is selective is desired, it is possible either:

preferably, to use only the stoichiometric amount (plus or minus 10 %) required for the first deallylation;

to chose a poorly nucleophilic receiver;

to chose pnictines of low completing capacity;

to perform the reaction at low temperature;

or, lastly, to combine all or some of the above measures. The first measure is generally preferred.

This surprising selectivity makes it possible to perform syntheses which were hitherto difficult. Thus, the synthesis of a variously trisubstituted amine may be performed starting from a diallylated amine (which may be obtained either by the action of allylating agent on a primary amine or the action of alkylating agent on a diallylamine, in general diallylamine itself)

by performing a selective monodeallylation according to the present invention by grafting a new radical onto the amine by releasing the second allylic function optionally, by grafting another radical onto the secondary amine thus formed.

The process according to the invention respects the geometry of the molecules and is, accordingly, particularly well suited to the chemistry of chiral molecules.

The non-limiting examples which follow illustrate the invention.

Definitions $DC$ = Degree of Conversion:

$$DC = \frac{\text{number of moles of product converted}}{\text{number of moles of initial product}}$$

$RY$ = yield based on the initial product $$RY = \frac{\text{number of moles of final product}}{\text{number of moles of initial product}}$$

$CY$ = the yield based on the product converted $$CY = \frac{\text{number of moles of final product}}{\text{number of moles of product converted}}$$

DEPROTECTION IN A WEAKLY AQUEOUS ONE-PHASE MEDIUM

General procedure

The catalyst is preformed by stirring $Pd(dba)_2$ and the coordinating agent diphenylphosphinobutane (DPPB) (1:1) in 1 ml of anhydrous THF (2.5 to 5% of catalyst for the reaction), for 15 minutes under argon. A brown-red solution is thus obtained.

The substrate to be deprotected (100 to 500 mg) and 3 ml of anhydrous THF are introduced into a tube, under argon. The nucleophile (sulphur-containing compound) or diethylamine (degassed) and, finally, the preformed catalytic system are then added.

If the nucleophile is diethylamine, the reaction medium is filtered through silica gel (eluent: EtOAc/cyclohexane (1:1). The filtrate is then concentrated under reduced pressure.

If the nucleophile is 2-mercaptobenzoic acid, it may be separated from the deprotected product by treatment with a basic solution (10% NaOH) during an extraction with ethyl acetate. The organic phase is dried and then concentrated. The deprotected products may be purified by chromatography on silica gel or may be distilled.

EXAMPLE 1

The above procedure was followed for methylallylbenzylamine, using 2-mercaptobenzoic acid as nucleophile.

After 15 minutes at room temperature, 81% (RY=81%; CY=100%; DC=81 %) of the substrate was freed.

EXAMPLE 2

The procedure of Example 1 was applied under the conditions indicated in the four tables below. The results are collated in these same tables.

TABLE 1

Deprotection of allylamines derived from secondary amines

| | Substrate | Product | Time | Yield (%) |
|---|---|---|---|---|
| 1. | Ph-N(CH₃)-allyl | Ph-NH-CH₃ | 25 min | 100 |
| 2. | Allyl ester of N-allyl-piperidine-4-carboxylate | piperidine-4-carboxylic acid | 40 min | 97(*) |
| 3. | Allyl-piperazine-CH₂CH₂OH | H-piperazine-CH₂CH₂OH | 30 min | 100 |
| 4. | Ph-N(Bu)-allyl | Ph-NH-Bu | 15 min | 100 |
| 5. | Ph-CH(*)-N(Bu)-allyl | Ph-CH(*)-NH-Bu | 10 min | 93 |
| 6. | Ph₂CH-N(Bu)-allyl | Ph₂CH-NH-Bu | 15 min | 100 |
| 7. | N-allyl proline methyl ester | proline methyl ester | 15 min | 100 |

(*)2 eq of 2-mercaptobenzoic acid are used

TABLE 2

Total deallylation of mono- and diallylamines

R—N(R')—CH₂CH=CH₂ →[Pd(dba)₂-DPPB, 5 mol %][THF, 55–60° C.] R—NH₂ + 2-(allylthio)benzoic acid (a) R' = H, 2-mercaptobenzoic acid 1.1 eq
(b) R' = allyl, 2-mercaptobenzoic acid 2.1 eq

| | Substrate | Product | Time | Yield (%) |
|---|---|---|---|---|
| 1. | PhCH₂-NH-allyl | PhCH₂-NH₂ | 30 min | 100 |
| 2. | Ph-CH(CH₃)-NH-allyl | Ph-C(=CH₂)-NH₂ | 15 min | 100 |
| 3. | Ph₂CH-NH-allyl | Ph₂CH-NH₂ | 20 min | 100 |
| 4. | PhCH₂-CH(N(allyl)₂)-CO₂Et | PhCH₂-CH(NH₂)-CO₂Et | 15 min | 100 |
| 5. | 4-methylcyclohexyl-N(allyl)₂ | 4-methylcyclohexyl-NH₂ | 30 min | 97 |
| 6. | Ph-CH=CH-CH₂-N(allyl)₂ | Ph-CH=CH-CH₂-NH₂ | 30 min | 100 |

TABLE 3

Selective monodeprotection of diallylamines

R—N(allyl)₂ →[Pd(O), 5 mol %, Room temp.][2-mercaptobenzoic acid, 1.1 eq, THF] R—NH-allyl

| | Substrate | Product | Time | Yield (%) |
|---|---|---|---|---|
| 1. | PhCH₂-N(allyl)₂ | PhCH₂-NH-allyl | 30 min | 100 |

TABLE 3-continued

Selective monodeprotection of diallylamines

| | Substrate | Product | Time | Yield (%) |
|---|---|---|---|---|
| 2. | PhCH(CH₃)–N(allyl)₂ | PhCH(CH₃)–NH(allyl) | 20 min | 100 |
| 3. | 4-methylcyclohexyl–N(allyl)₂ | 4-methylcyclohexyl–N(allyl)₂ | 30 min | 100 |
| 4. | 1,4-bis(diallylamino)cyclohex-2-ene | 1,4-bis(allylamino)cyclohex-2-ene | 90 min | 98 |
| 5. | PhCH=CHCH(Ph)–N(allyl)₂ | PhCH=CHCH(Ph)–NH(allyl) | 30 min | 70 |
| 6. | PhCH=CHCH₂–N(allyl)₂ | PhCH=CHCH₂–NH(allyl) | 45 min | 93 |
| 7. | Leu-OMe–N(allyl)₂ | Leu-OMe–NH(allyl) | 30 min | 72 |
| 8. | Phe-OEt–N(allyl)₂ | Phe-OEt–NH(allyl) + Phe-OEt–NH₂ (82:18) | 15 min | — |

Pd(O) = Pd(dba)₂-DPPB

TABLE 4

Chemoselective deprotections of hydroxy amine molecules

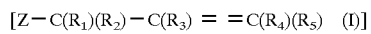

| | Substrate | Step (1) Product | Time/Yield (%) | Step (2) Product | Time/Yield (%) |
|---|---|---|---|---|---|
| 1. | [piperazine with N-allyl and N-CH2CH2-O-C(O)-O-allyl] | [piperazine with N-allyl and N-CH2CH2-OH] | 30 min/100 | [piperazine with NH and N-CH2CH2-OH] | 30 min/100 |
| 2. | [4-Ph-4-(O-C(O)-O-allyl)-1-allyl-piperidine] | [4-Ph-4-OH-1-allyl-piperidine] | 45 min/100 | [4-Ph-4-OH-piperidine NH] | 30 min/100 |
| 3. | [Ph-CH(O-C(O)-O-allyl)-CH(CH3)-N(CH3)(allyl)] | [Ph-CH(OH)-CH(CH3)-N(CH3)(allyl)] | 15 min/98 | [Ph-CH(OH)-CH(CH3)-NH(CH3)] | 15 min/100 |

Pd(O) = Pd(dba)$_2$-DPPB

We claim:

1. A process for the treatment of a molecule containing at least one allylic function other than ester, comprising reacting said molecule with a reagent in order to remove the allylic function wherein said reagent comprises:
   a) a solvent system;
   b) a catalyst containing at least one element from column VIII of the Periodic Table of the Elements, said element from column VIII of the Periodic Table being coordinated with at least one coordination agent which is soluble in said solvent system, wherein said coordination agent is a pnictine; and
   c) a compound which is at least partially soluble in said solvent system and which contains at least one nucleophilic function, wherein said nucleophile is soft and has a nucleophilicity which is at least equal to that of diethylamine, and further wherein said nucleophile presents a function which corresponds to atoms from a row of the Periodic Table at least equal to the third.

2. The process according to claim 1, wherein said molecule containing at least one allylic function corresponding to the following formula (I):

$$[Z-C(R_1)(R_2)-C(R_3)==C(R_4)(R_5)] \quad (I)$$

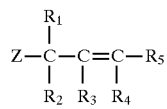

where $R_1$ represents a hydrogen or an alkyl radical;

$R_2$ represents a hydrogen or an alkyl radical;

$R_3$ represents a hydrogen or an alkyl radical, or, with $R_4$, forms an additional double bond;

$R_4$ represents a hydrogen or an alkyl radical, or, with $R_3$, forms an additional double bond;

$R_5$ represents a hydrogen or an alkyl radical, or an aryl radical;

Z being the radical derived from the molecule to protect the bond replacing a hydrogen of the function whose protection is desired, Z contains the protected molecule, which needs to be freed of its protecting group;

with the condition that Z does not form an allylic ester function with the residue of the molecule

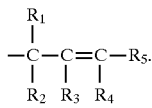 (II)

3. The process according to claim 1, wherein said process is part of a peptide synthesis.

4. The process according to claim 1, wherein said process is part of a synthesis of nucleotides or of nucleosides.

5. The process according to claim 1, wherein said process is part of an amine synthesis.

6. The process according to claim 1, wherein the amount of said nucleophile is at least equal to 3/2 times the amount required stoichiometrically.

7. The process according to claim 1, wherein the amount of said nucleophile is at least equal to a value of between 0.9 and 1.1 times the amount required stoichiometrically.

8. The process according to claim 1, wherein said nucleophile has an acid function.

9. The process according to claim 1, wherein said nucleophile has a nucleophilic function which itself has a sulphur atom as the nucleophilic atom.

10. The process according to claim 2, wherein $R_1$ is an alkyl radical containing 1 or 2 carbon atoms.

11. The process according to claim 2, wherein $R_2$ is an alkyl radical containing 1 or 2 carbon atoms.

12. The process according to claim 2, wherein $R_3$ is an alkyl radical containing 1 or 2 carbon atoms.

13. The process according to claim 2, wherein $R_4$ is an alkyl radical containing 1 or 2 carbon atoms.

14. The process according to claim 2, wherein $R_5$ is an alkyl radical containing 1 or 2 carbon atoms.

15. A reagent which is useful for cleaving an allylic protecting group from a molecule, said reagent comprising:
a) a solvent system;
b) a catalyst containing at least one element from column VIII of the Periodic Table of the Elements, said element from column VIII of the Periodic Table being coordinated with at least one coordination agent which is soluble in said solvent system, wherein said coordination agent is a pnictine; and
c) a compound which is at least partially soluble in said solvent system and which contains at least one nucleophilic function, wherein said nucleophile is soft and has a nucleophilicity which is at least equal to that of diethylamine.

16. The reagent according to claim 15, wherein said coordination agent is a phosphine.

17. The reagent according to claim 15, wherein said coordination agent is selected from the group consisting of bis(cyclohexyl-phosphine) and tris(cyclohexylphosphine).

18. The reagent according to claim 15, wherein the amount of said nucleophile is at least equal to 3/2 times the amount required stoichiometrically.

19. The reagent according to claim 15, wherein the amount of said nucleophile is equal to a value of between 0.9 and 1.1 times the amount required stoichiometrically.

20. The reagent according to claim 15, wherein said nucleophile is an acid having a sulphide function.

21. The reagent according to claim 16, wherein said coordination atoms are trivalent hydrocarbon derivatives of elements ranking higher than the second line of column VB of the Periodic Table of the Elements.

22. The reagent according to claim 17, wherein said pnictine is a trialkylphosphine.

23. The reagent according to claim 17 wherein said pnictine is a triarylphophine.

24. A reagent according to claim 15, wherein in addition to the nucleophile function the nucleophilic compound further comprises a strong or medium-strength acid function with a pKa no greater than 6.

25. A reagent according to claim 24, wherein in addition to the nucleophile function the nucleophilic compound further comprises a strong or medium-strength acid function with a pKa no greater than 5.

26. A reagent according to claim 25, wherein in addition to the nucleophile function the nucleophilic compound further comprises a strong or medium-strength acid function with a pKa no greater than 4.

27. A reagent according to claim 15, wherein the nucleophilic function is carried by a carbon which is vicinal to that carrying the acidic function.

28. A reagent according to claim 15, wherein the nucleophilic function is carried by a carbon which is postvicinal to that carrying the acidic function.

* * * * *